(12) United States Patent
Pynson (10) Patent No.: US 8,603,163 B2
(45) Date of Patent: Dec. 10, 2013

(54) APPARATUS AND METHODS FOR LOADING OF AN IOL INJECTOR

(75) Inventor: Joel Pynson, Toulouse (FR)

(73) Assignee: Bausch & Lomb Incorporated, Rochester, NY (US)

( * ) Notice: Subject to any disclaimer, the term of this patent is extended or adjusted under 35 U.S.C. 154(b) by 3 days.

(21) Appl. No.: 13/027,722

(22) Filed: Feb. 15, 2011

(65) Prior Publication Data

US 2011/0137321 A1   Jun. 9, 2011

Related U.S. Application Data

(63) Continuation of application No. 11/316,457, filed on Dec. 22, 2005, now abandoned.

(51) Int. Cl.
*A61F 2/16* (2006.01)

(52) U.S. Cl.
USPC .......................................... 623/6.12

(58) Field of Classification Search
USPC ................. 606/166; 623/6.12, 6.13
See application file for complete search history.

(56) References Cited

U.S. PATENT DOCUMENTS

| | | | |
|---|---|---|---|
| 2,397,823 A | 4/1946 | Walter |
| 4,257,521 A | 3/1981 | Poler |
| 4,267,717 A | 5/1981 | Martikainen |
| 4,573,998 A | 3/1986 | Mazzocco |
| 4,681,102 A | 7/1987 | Bartell |
| 4,697,697 A | 10/1987 | Graham et al. |
| 4,897,981 A | 2/1990 | Beck |
| 4,976,716 A | 12/1990 | Cumming |
| 5,111,946 A | 5/1992 | Glanz |
| 5,123,905 A | 6/1992 | Kelman |
| 5,176,686 A | 1/1993 | Poley |
| 5,304,182 A | 4/1994 | Rheinish et al. |
| 5,496,328 A | 3/1996 | Nakajima et al. |
| 5,947,975 A | 9/1999 | Kikuchi et al. |
| 6,048,347 A | 4/2000 | Erdman |
| 6,183,513 B1 | 2/2001 | Guenthner et al. |
| 6,387,101 B1 | 5/2002 | Butts et al. |
| 6,447,519 B1 | 9/2002 | Brady et al. |

(Continued)

FOREIGN PATENT DOCUMENTS

| | | |
|---|---|---|
| DE | 202 19 445 U1 | 3/2003 |
| DE | 20219445 | 4/2003 |

(Continued)

OTHER PUBLICATIONS

Staar Surgical, "Microstaar Injector Package Insert".

(Continued)

*Primary Examiner* — Thomas McEvoy
(74) *Attorney, Agent, or Firm* — Toan P. Vo (57) ABSTRACT

An IOL injector body including an injector body segment defining a portion of a lumen, and a first loading chamber component coupled to the injector body segments and a second loading chamber component hingedly coupled to the first loading chamber component. The second loading chamber component is capable of rotating about an axis that is parallel to the lumen. An IOL vial including a vial base and an injector guide rotatably mounted in said base, whereby an injector can be inserted along the injector guide and rotated such that a folded IOL can be obtained in the injector. A method of loading an IOL injector with an IOL the method that comprises inserting the IOL injector body into a vial and rotating the IOL injector body relative to the vial to obtain the IOL in the IOL injector body.

10 Claims, 13 Drawing Sheets

(56) References Cited

U.S. PATENT DOCUMENTS

| | | |
|---|---|---|
| 6,468,282 B2 | 10/2002 | Kikuchi et al. |
| 6,537,283 B2 | 3/2003 | Van Noy |
| 6,540,754 B2 | 4/2003 | Brady |
| 6,558,395 B2 | 5/2003 | Hjertman et al. |
| 7,226,455 B2 | 6/2007 | Jeannin et al. |
| 2006/0036262 A1 | 2/2006 | Hohl |
| 2007/0060925 A1 | 3/2007 | Pynson |
| 2007/0095700 A1 | 5/2007 | Peterseon et al. |
| 2007/0150055 A1 | 6/2007 | Pynson |
| 2007/0168026 A1 | 7/2007 | Nagasaka |

FOREIGN PATENT DOCUMENTS

| | | |
|---|---|---|
| DE | 10234290 A1 | 5/2004 |
| DE | 202004017931 U1 | 2/2005 |
| WO | WO 03/044946 A2 | 5/2003 |
| WO | WO 2005/030097 | 4/2005 |
| WO | WO 2005/082284 | 9/2005 |

OTHER PUBLICATIONS

Medicel, AG, "Naviject Single-Use Product Description," Medicelag.com (Aug. 10, 2006).

International Preliminary Report on Patentability in corresponding PCT dated Jun. 25, 2008.

International Search Report and Written Opinion of the International Searching Authority in corresponding PCT dated Nov. 7, 2007.

International Search Report and Written Opinion of the International Searching Authority in PCT related application (PCT/US2006/046930) dated Nov. 7, 2007.

International Preliminary Report on Patentability in PCT related application (PCT/US2006/046930) dated May 26, 2008.

APPARATUS AND METHODS FOR LOADING OF AN IOL INJECTOR

CROSS REFERENCE

This application is a continuation of application Ser. No. 11/316,457, filed Dec. 22, 2005 which is incorporated by reference herein.

FIELD OF INVENTION

The present invention relates to intraocular lens (IOL) injectors, and more particularly to loading apparatus and methods for IOL injectors.

BACKGROUND OF THE INVENTION

IOLs are artificial lenses used to replace natural crystalline lenses of eyes when the natural lenses are diseased or otherwise impaired. Under some circumstances a natural lens may remain in an eye together with an implanted IOL. IOLs may be placed in either the posterior chamber or anterior chamber of an eye.

IOLs come in a variety of configurations and materials. Various instruments and methods for implanting such IOLs in an eye are known. Typically, an incision is made in a patient's cornea and an IOL is inserted into the eye through the incision. In one technique, a surgeon uses surgical forceps having opposing blades to grasp the IOL and insert it through the incision into the eye. While this technique is still practiced today, more and more surgeons are using IOL injectors which offer advantages such as affording a surgeon more control when inserting an IOL into an eye and permitting insertion of IOLs through smaller incisions. Smaller incision sizes (e.g., less than about 3 mm) are preferred over larger incisions (e.g., about 3.2 to 5+mm) since smaller incisions have been attributed to reduced post-surgical healing time and reduced complications such as induced astigmatism.

In order for an IOL to fit through a smaller incision, it is typically folded and/or compressed prior to entering the eye where they will assume their original unfolded/uncompressed shape. Since IOLs are very small and delicate articles of manufacture, great care must be taken in their handling, both as they are loaded into an injector and as the lens is injected into a patient's eye.

It is important that an IOL be expelled from the tip of the IOL injector and into the eye in an undamaged condition and in a predictable orientation. Should an IOL be damaged or expelled from the injector in an incorrect orientation, a surgeon must remove or further manipulate the IOL in the eye, possibly resulting in trauma to the surrounding tissues of the eye. To achieve proper delivery of an IOL, consistent loading of the IOL into the injector device with a minimum opportunity for damaging the IOL is desirable.

Various IOL injectors and other devices have been proposed which attempt to address issues related to loading, yet there remains a need for an IOL injector which improves consistency of loading and reduces the likelihood of damage to an IOL.

SUMMARY

Aspects of the present invention are directed to an IOL injector comprising a loading chamber comprising a component that when being closed folds the lens. Additional aspects of the present invention are directed to a vial for maintaining an IOL prior to loading. The vial includes an injector guide that receives an injector such that when the injector is rotated a folded IOL can be obtained in the injector. In some embodiments, the injector and vial are provided in a combination. As defined here in "a combination" includes but is not limited to arrangements in which the objects in the combination are packaged and are not connected to one another.

Other aspects of the present invention are directed to an injector having an opening to a loading chamber, the opening being defined by a tapered edge. Additional aspects of the present invention are directed to an IOL vial comprising a convexly curved interior surface and a flexible arm adapted to maintain an IOL against a surface opposite the convexly curved interior surface. In some embodiments, the injector having tapered edge and the vial having a flexible arm are provided in a combination.

A first aspect of the invention is directed to an IOL injector body having a lumen with a longitudinal axis, the IOL injector comprising an injector body segment defining a portion of the lumen; a first loading chamber component coupled to the injector body segment; and a second loading chamber component comprising a lens contact surface, the second loading chamber component being hingedly coupled to the first loading chamber component such that the second loading chamber component is capable of rotating about a second axis that is parallel to the longitudinal axis.

In some embodiments, the second loading chamber component is configured and arranged such that, upon rotation of the second loading chamber about the second axis, the first loading chamber component and the second loading chamber component combine to form a second portion of the lumen. In some embodiments, the first and second loading chamber components form a rotationally complete portion of the lumen. In some embodiments, the second loading component is configured and arranged to fold an IOL using the lens contact surface upon rotation about the second axis. In some embodiments, the second loading component is configured and arranged to fold the IOL such that after rotation the lens is ready for delivery.

The second axis may be aligned with a wall of the injector body. In some embodiments, the first loading chamber component is rigidly connected to the injector body; In some embodiments, the first loading chamber component is integrally formed with the injector body. The first loading chamber component and the second loading chamber component may be configured to maintain the loading chamber in a closed position. The first loading chamber component and the second loading chamber component may be configured to snap together. The injector may be in a combination with a vial comprising a vial base, an IOL-holder mount disposed in said base, and an injector guide rotatably mounted in said base.

Another aspect of the invention is directed to a IOL vial, comprising: a vial base; an IOL-holder mount disposed in said base; and an injector guide rotatably mounted in said base, whereby an injector can be inserted along the injector guide and rotated. The injector guide may be disposed on a guide support. In some embodiments, the guide support is cylindrical.

In some embodiments the IOL-holder mount may be comprised of a first prong and a second prong, the first prong and the second prong being separated from one another. The vial may further comprise a second IOL-holder mount. The second IOL-holder mount may be comprised of a third prong and a fourth prong, the third prong and the fourth prong being separated from one another.

The vial may be in a combination with a lens holder, the lens holder being disposed between the first and second prong, and between the third prong and the fourth prong. The first holder mount and the second holder mount, and the lens holder may be configured such that the lens holder is capable of being slidably held by first holder mount and the second holder mount.

The term "lens contact surface" is defined herein as a surface arranged to contact an IOL lens after the loading chamber is closed. An injector having an IOL that is "ready for delivery" is an injector that is in a condition such that actuation of its IOL ejection apparatus (e.g., a plunger) results in ejection of the IOL from the injector.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1A:
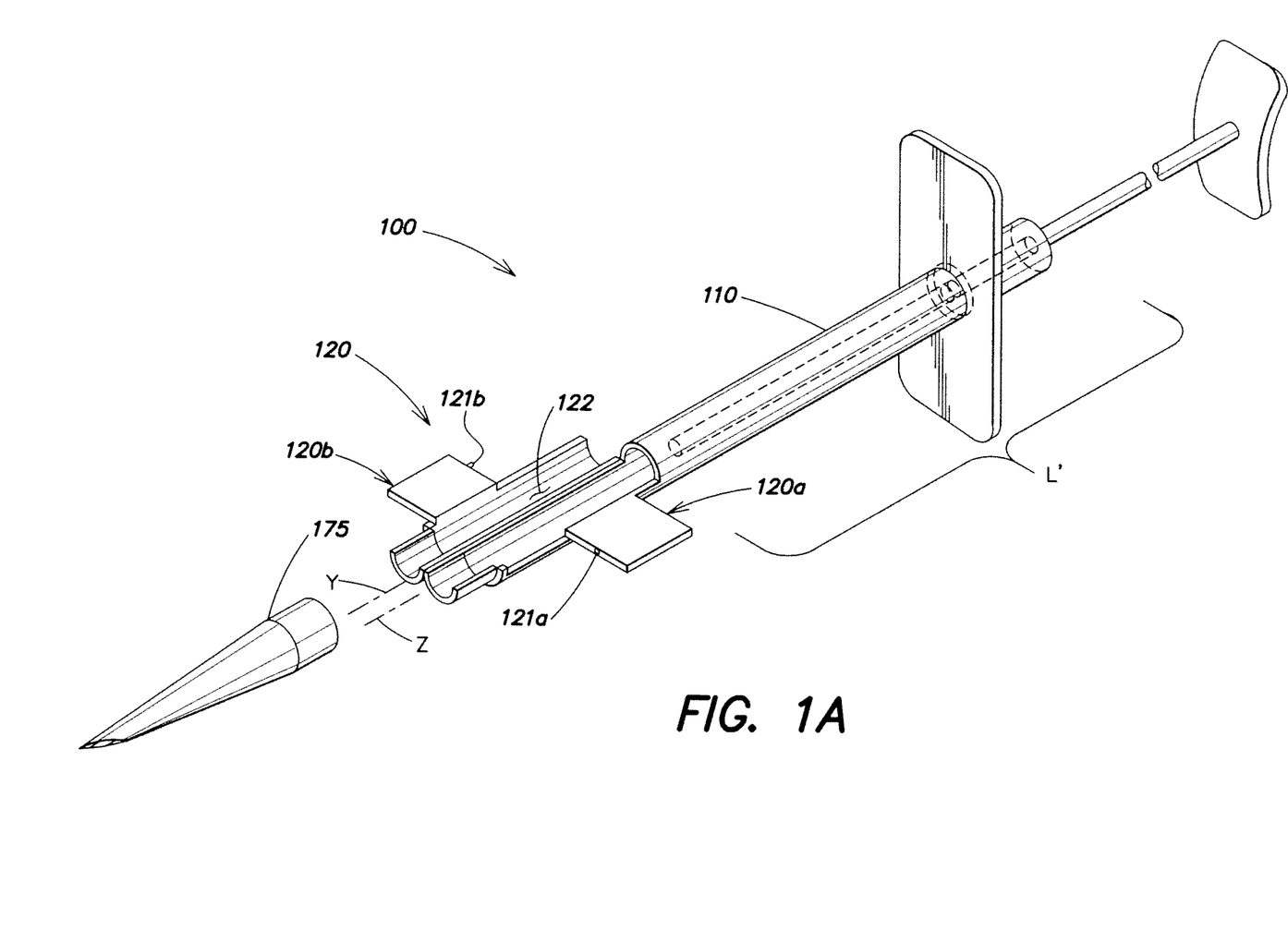
FIG. 1A is a perspective view of an exemplary embodiment of an injector according to aspects of the present invention having an open loading chamber.

FIG. 1A is a perspective view of an exemplary embodiment of an IOL injector 100 according to aspects of the present invention. As illustrated in FIG. 1A, IOL injector 100 has an open loading chamber and a detached tip 175. Injector 100 includes a lumen having a longitudinal axis Z. An injector body segment 110 defines a portion L' of the lumen. As described below, another portion of the lumen is provided by the loading chamber 120 when it is closed.

Figure 1B:
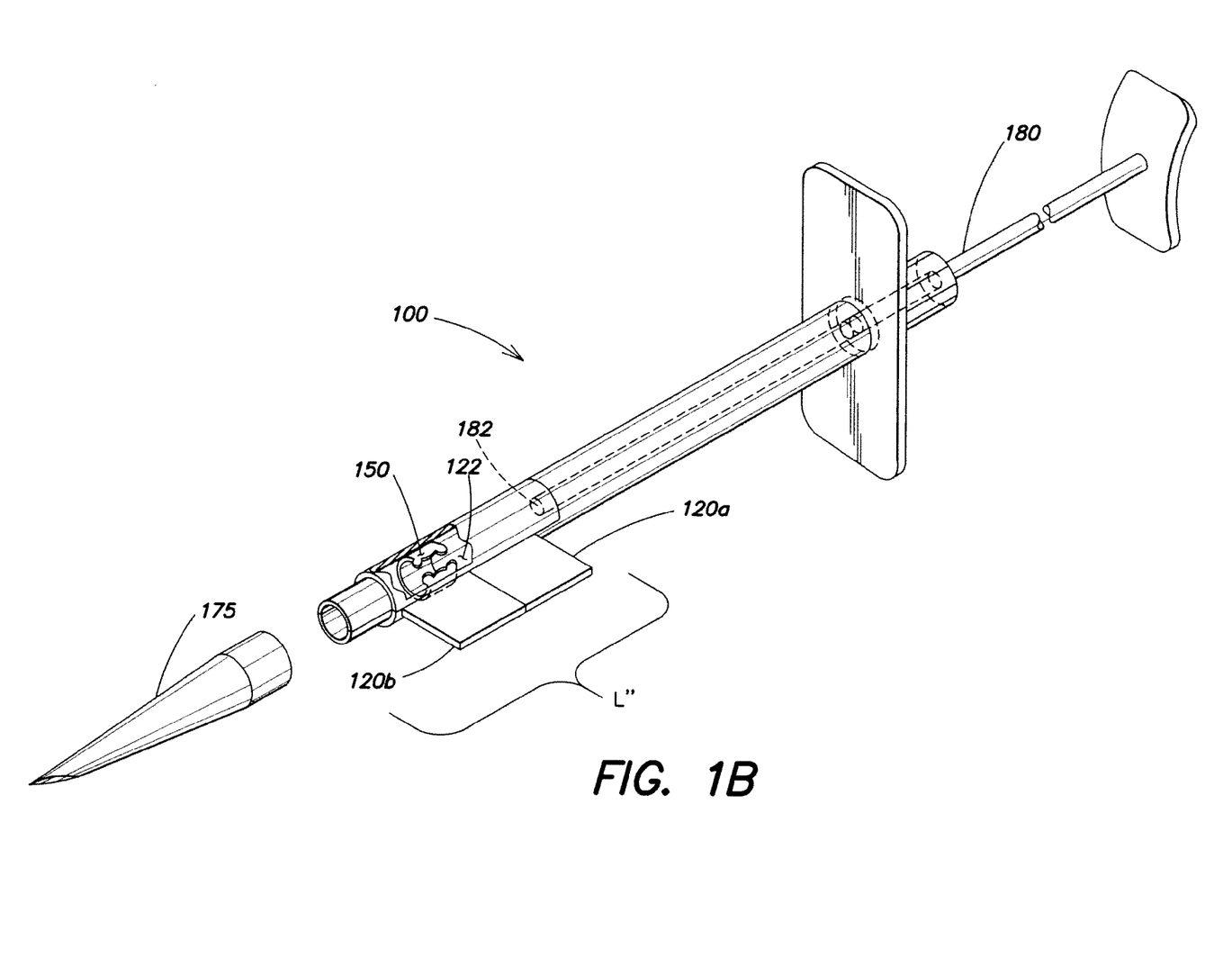
FIG. 1B is a perspective view of an exemplary embodiment of a injector according to aspects of the present invention having a closed loading chamber.
Figure 1C:
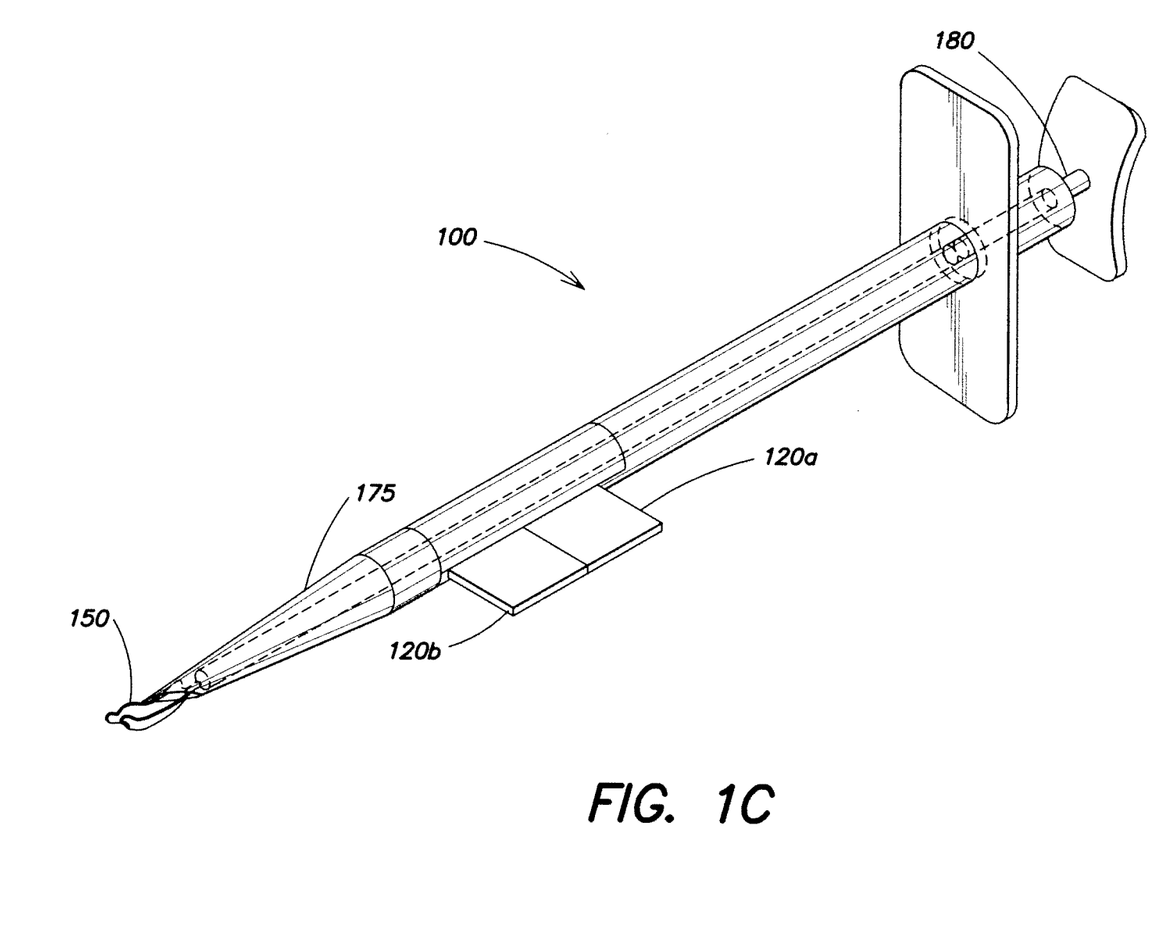
FIG. 1C is a perspective view of an exemplary embodiment of a injector according to aspects of the present invention having a tip attached.

A first loading chamber component 120a is coupled to the injector body segment; and a second loading chamber component 120b is hingedly coupled to the first loading chamber component such that the second loading chamber component is capable of rotating about a second axis Y that is parallel to longitudinal axis Z. In some embodiments, the second axis may be aligned with a wall of the injector body as illustrated in FIGS. 1A-1C. However, coincidence is not necessary and the second axis may be offset from the wall of the lumen.

First loading chamber component 120a may be coupled to injector body 100 segment 110 in any suitable manner. For example, the first loading chamber component may be rigidly connected to the injector body. In some embodiments, the first loading chamber component may be integrally formed (e.g., molded as a single part) with the injector body segment. Other suitable techniques of attachment include, but are not limited to snap fit or compression fit or by using a connector such as a screw or other threaded structure.

As illustrated in FIG. 1B, when second loading chamber component 120b is rotated about second axis Y such that the loading chamber is closed, the first loading chamber component and the second loading chamber component combine to form a second portion L" of the lumen. Preferably, the first loading chamber component and the second loading chamber component fixedly couple together when the loading chamber is closed such that they maintain a closed loading chamber after rotation of the second loading chamber component. For example, a molded snap fit structure may be provided on the first and second loading chamber components (i.e., they are configured to snap together). As illustrated in FIG. 1A, in some embodiments, the snap fit structure may comprise a projection 121b on one of the bottom surface of first loading chamber component and the top surface of second loading chamber component, and a detent 121a on the other of bottom surface 121a and top surface 121a.

Also as illustrated in FIGS. 1A and 1B, second loading chamber component 120b comprises a lens contact surface 122. It is to be appreciated that in the illustrated embodiment the second loading chamber component is configured and arranged to fold an IOL 150 (also referred to herein simply as a "lens"), using the lens contact surface, upon rotation of the second loading chamber component about second axis Y. As illustrated in FIG. 1B, in some embodiments, the first and second loading chamber components form a rotationally complete portion L" of the lumen.

Upon rotation of the second loading chamber component, IOL 150 is located in loading chamber ready for delivery (i.e., the lens is located such that upon depressing of plunger 180, IOL 150 is expelled from the injector). Plunger 180 is aligned in the lumen such that tip 182 advances the lens after it has been obtained in the injector. The tip may be conventional fork shaped tip or a soft silicone tip as is known in the art. As illustrated in FIG. 1C, according some embodiments of the invention, upon rotation of the second loading chamber component, such that the loading chamber is closed, a tip 175 may be attached to an end of the injector body.

Figure 2A:
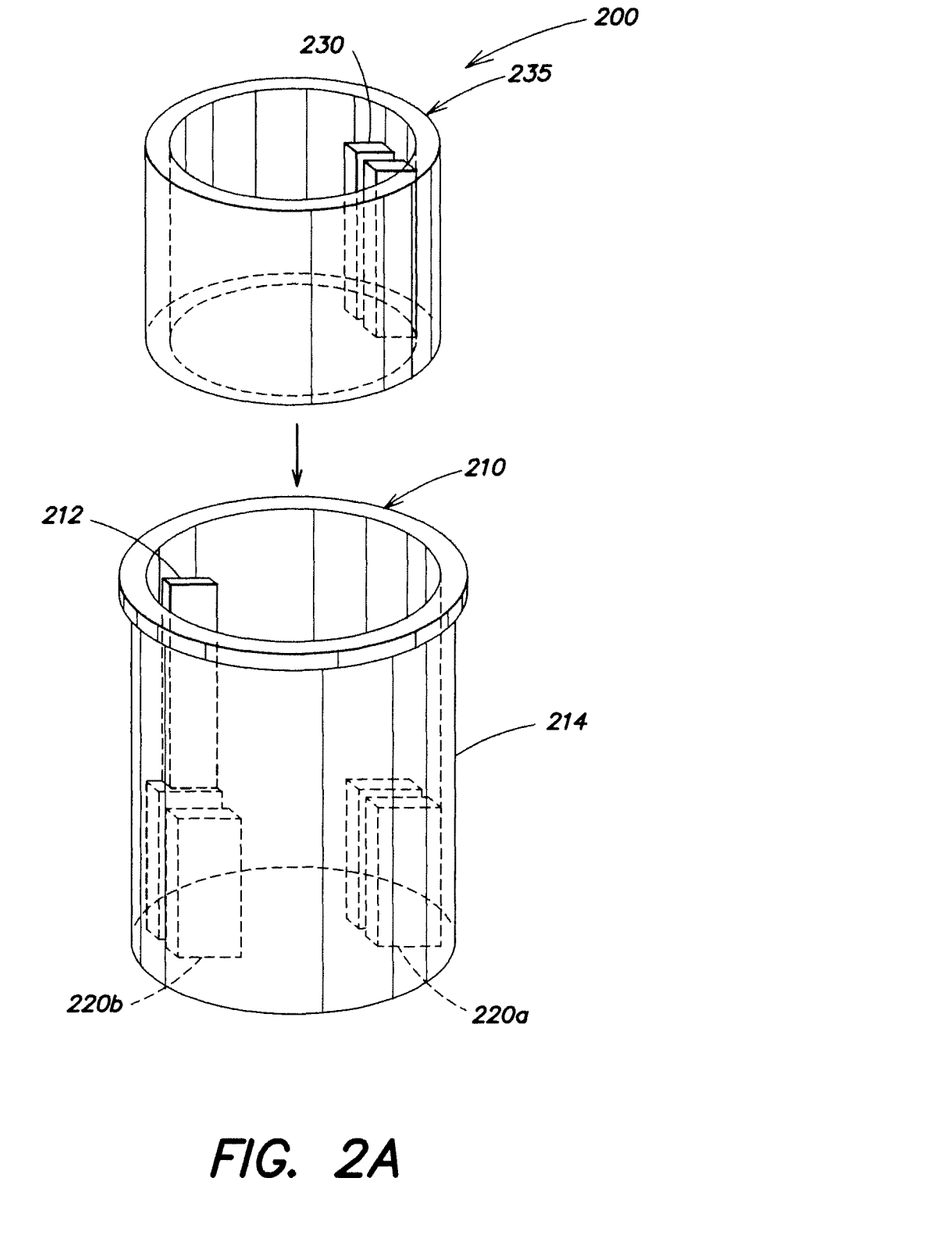
FIG. 2A is a perspective view of an exemplary embodiment of a vial according to aspects of the present invention.

FIG. 2A is a perspective view of an exemplary embodiment of an IOL vial 200 according to aspects of the present invention. Vial 200, comprises a vial base 210, and an IOL holder mount including a first support 220a and a second support 220b disposed in the vial base. Vial 200 also includes an injector guide 230 that is configured to be rotatably mounted in the vial base. As discussed in greater detail below with reference to FIGS. 5A-5C, an IOL injector (e.g., injector 100 illustrated in FIG. 1A) can be inserted along injector guide 230 and rotated such that a folded IOL can be obtained in the injector. As illustrated in FIG. 2A, injector guide 230 may be coupled to a guide support 235 that maintains injector guide 230 relative to vial base and supports 220a and 220b. As discussed in greater detail below with reference to FIG. 5B, the guide support 235 extends below the bottom of guide 230.

It is to be appreciated that, in the illustrated embodiment, guide support 235 is cylindrical so as to conform to the shape of the vial base. The guide support may form a continuous cylinder or have a gap. Also, as illustrated in greater detail in FIG. 5A, guide support 235 is sized to fit between a sidewall 214 of the vial base and a fixed stop 212.

Figure 2B:
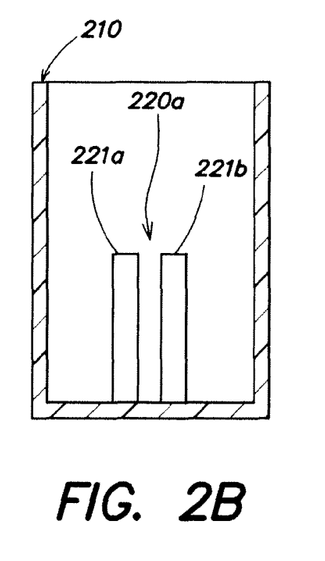
FIGS. 2B-C are side views of the exemplary embodiment of the vial illustrated in FIG. 2A.
Figure 2C:
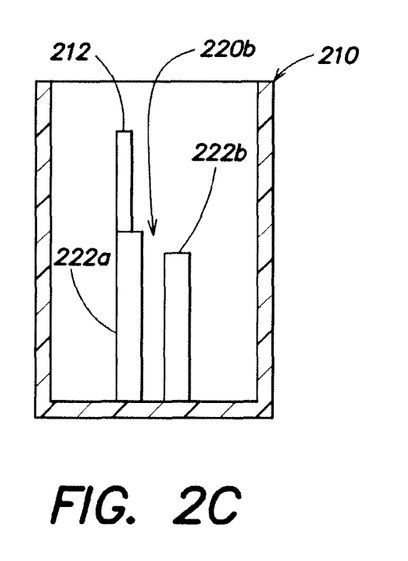

FIG. 2B illustrates holder mount 220a of a vial base 210 in greater detail. Holder mount 220a comprises a first prong 221a and a second prong 221b. FIG. 2C illustrates holder mount 220b of vial base 210 in greater detail. Holder mount 220b comprises a first prong 222a and a second prong 222b. In some embodiments, prong 222b is slightly lower than prong 222a. As described below, the space between prong 221a and prong 221b, and the space between prong 222a and prong 222b are selected so that holder mounts 220a and 220b slidably hold a lens holder as described in greater detail below.

Figure 3A:
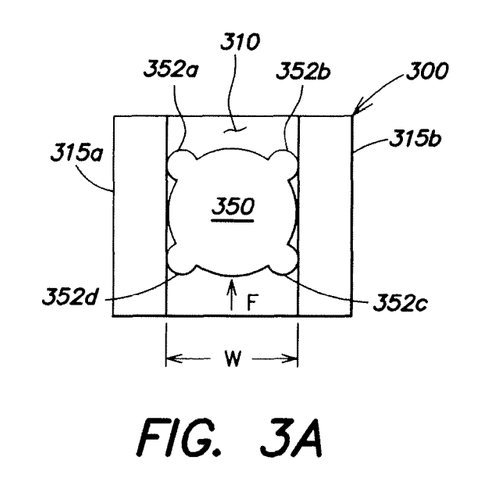
FIG. 3A is a plan view of an exemplary embodiment of a lens holder according to aspects of the present invention.
Figure 3B:
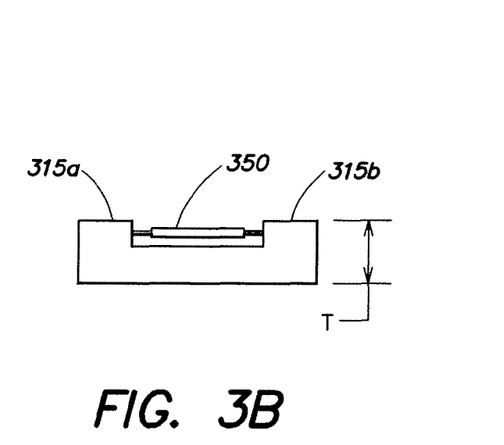
FIG. 3B is a side view of the exemplary embodiment of the lens holder illustrated in FIG. 3A.

FIGS. 3A and 3B illustrate an exemplary embodiment of a lens holder 300 suitable for use with the injector 100 and vial 200. An IOL 350 is disposed in a valley 310 between two ridges 315a and 315b. The width W of the valley is selected such that IOL 350 can be maintained between the ridges due to friction between the IOL haptics 352a-352d and the ridges 315a and 315b. Holder 300 has a thickness T at the ridges. As discussed below, IOL 350 may be removed from mount 300 by application a force F to a side of IOL 350 such that force F overcomes the friction holding IOL between the ridges. It is to be appreciated that any suitable IOL and IOL holder may be used with aspects of the present invention. For example, the IOL may have any suitable optic shape and may have any suitable number of haptics (e.g., one, two or three), and the IOL holder may have any suitable shape.

Figure 4:
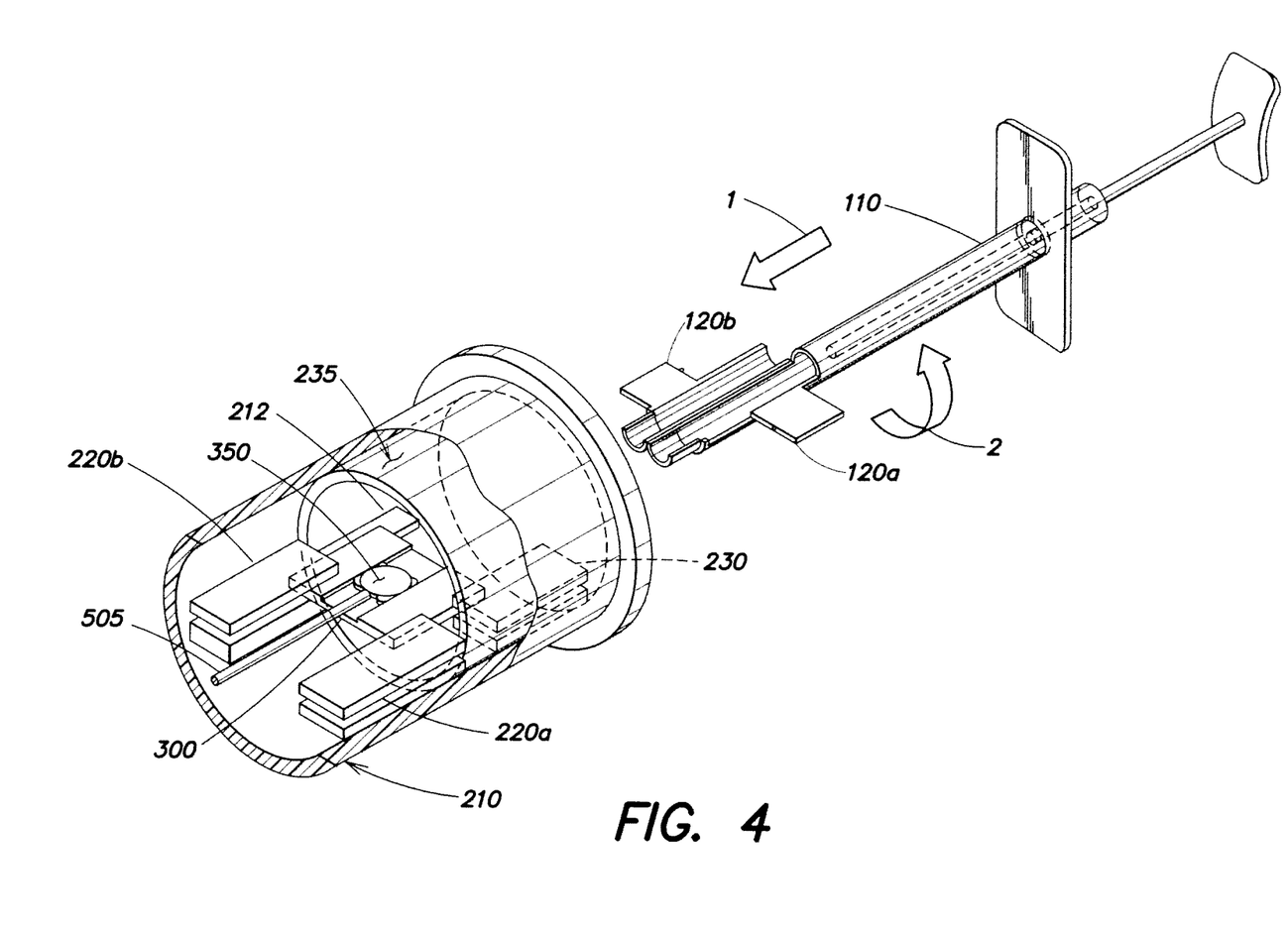
FIG. 4 is a perspective view of the exemplary embodiment of an injector as illustrated in FIG. 1A engaged with the exemplary embodiment of a vial as illustrated in FIG. 2A, in which a portion of the vial is broken away.

FIG. 4 is a perspective view of injector body 110 as illustrated in FIG. 1A engaged with the exemplary embodiment of a vial 200 as illustrated in FIG. 2A. As discussed above, injector body 110 can be inserted along injector guide 230 (in the direction indicated by arrow 1) and rotated (in the direction of arrow 2) such that a folded IOL 350 can be obtained in the injector body.

It is to be appreciated that although in some applications it is advantageous to provide and/or use injector 100 with a vial 200, injector 100 may be used with any suitable structure capable of maintaining an IOL such that the second loading chamber component can be used to interact with the IOL in a manner such that the IOL is obtained in loading chamber.

Figure 5A:
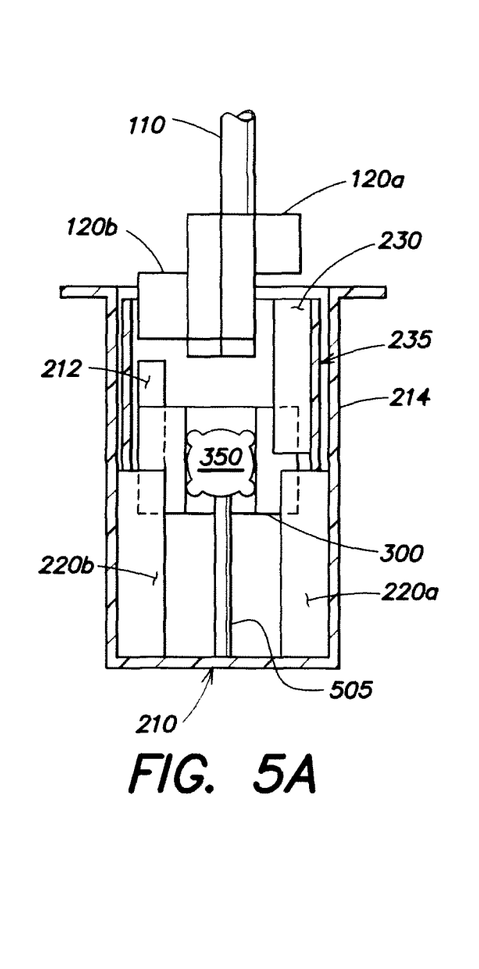
FIGS. 5A-5C illustrate steps for loading an injector according to aspects of the present invention.
Figure 5B:
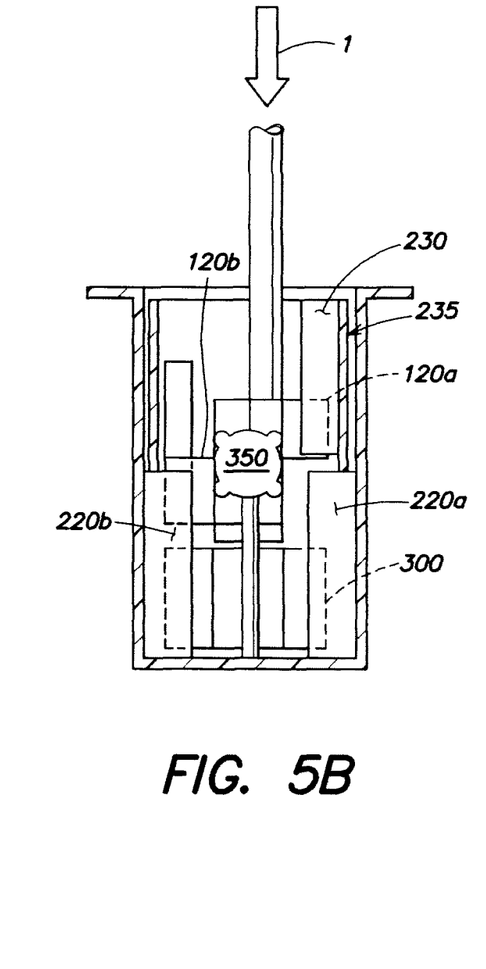
Figure 5C:
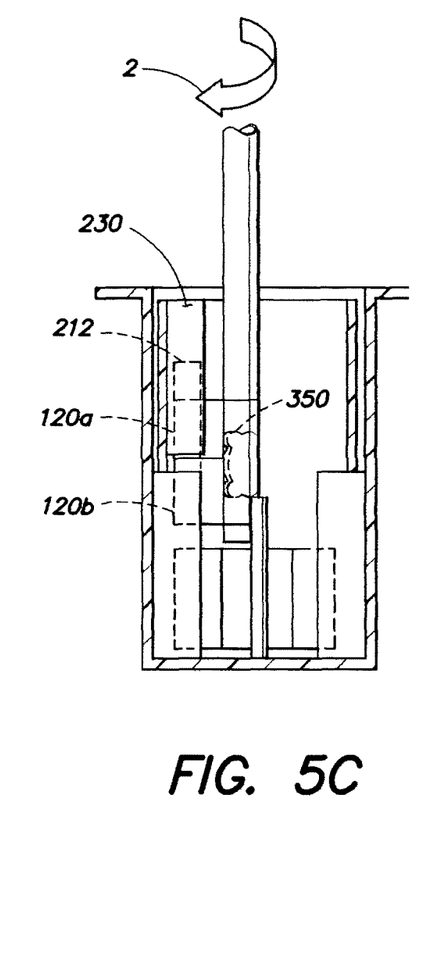

FIGS. 5A-5C illustrate an exemplary progression of steps for loading an injector body 110 with an IOL 350 according to aspects of the present invention. It is to be appreciated that only a portion of the injector body 110 proximate the loading chamber 120 is illustrated in FIGS. 5A-5C to avoid obfuscation.

As illustrated in FIG. 5A, IOL holder 300 is supported by IOL supports 220a and 220b of IOL holder support 220. A thickness T (see FIG. 3B) is sized relative to the distance between prongs 221a and 221b (see FIG. 2A), and the distance between prongs 222a and 222b (see FIG. 2B) so as to form a friction fit between prongs 221a and 221b of IOL support 220a and to form a friction fit between prongs 221a and 222b of IOL support 220b. Accordingly, lens holder 300 is slidably held by the supports 220a and 220b such that upon application of a force F' to the lens holder, IOL holder 300 slides between pair of prongs 221a, 222a and pair or prongs 221b, 222b toward the bottom of the vial. It is to be appreciated that as IOL holder 300 slides between the prongs, IOL 350 is contacted by a projection 505 such that a force F, which is capable of overcoming the friction between haptics 352a-352d and holder 300 (as described above with reference to FIG. 3A), is applied to lens 350. Lens 350 can thereby be detached from the holder 300. Projection 505 may be attached to or separate of vial base 210. Vial base 210 may be provided with a holder (not shown), such as a hollow cylinder, disposed on its bottom to facilitate positioning of projection 505. Fixed stop 212 is included in FIG. 5A for clarity.

FIG. 5B illustrates IOL holder 300 after it has been displaced in the direction of arrow 1 (i.e., toward the bottom of vial 300) a sufficient distance such that IOL 350 is completely detached from IOL holder 300 and is located proximate loading chamber 120 (i.e., the lens is proximate first loading chamber component 120a and second loading chamber 120b).

It is to be appreciated that, as illustrated in FIG. 5B, injector body 110 is pushed into the vial base 210 a distance such that first loading chamber component 120a is at least a small distance above holder mount 220a and a small distance below injector guide 230, thus exposing the bottom of first loading chamber component 120a. As discussed above, with reference to FIG. 2A, the guide support 235 extends below the bottom of injector guide 230. Accordingly, there is a separation between the bottom of guide 230 and the top of support 220a such that the bottom of first loading chamber component 120a is exposed during rotation.

Additionally, the top of second loading chamber component 120b extends above holder mount 220b, such that upon rotation of the injector (in the direction of arrow 2) as indicated in FIG. 5C, the bottom of first loading chamber component 120a and the top of second loading chamber component 120b contact one another and become attached to one another, for example using a snap fit as discussed above with reference to FIG. 1A. Accordingly, upon rotation of the injector body 110, the loading chamber is closed and a folded IOL 150 is achieved in injector 100. As discussed above with reference to FIG. 2C, second prong 222b may be slightly lower than prong 222a, thereby facilitating closure. In some embodiments, fixed stop 212 operates to prevent over rotation of the second loading chamber component relative to the first loading chamber component.

Figure 6A:
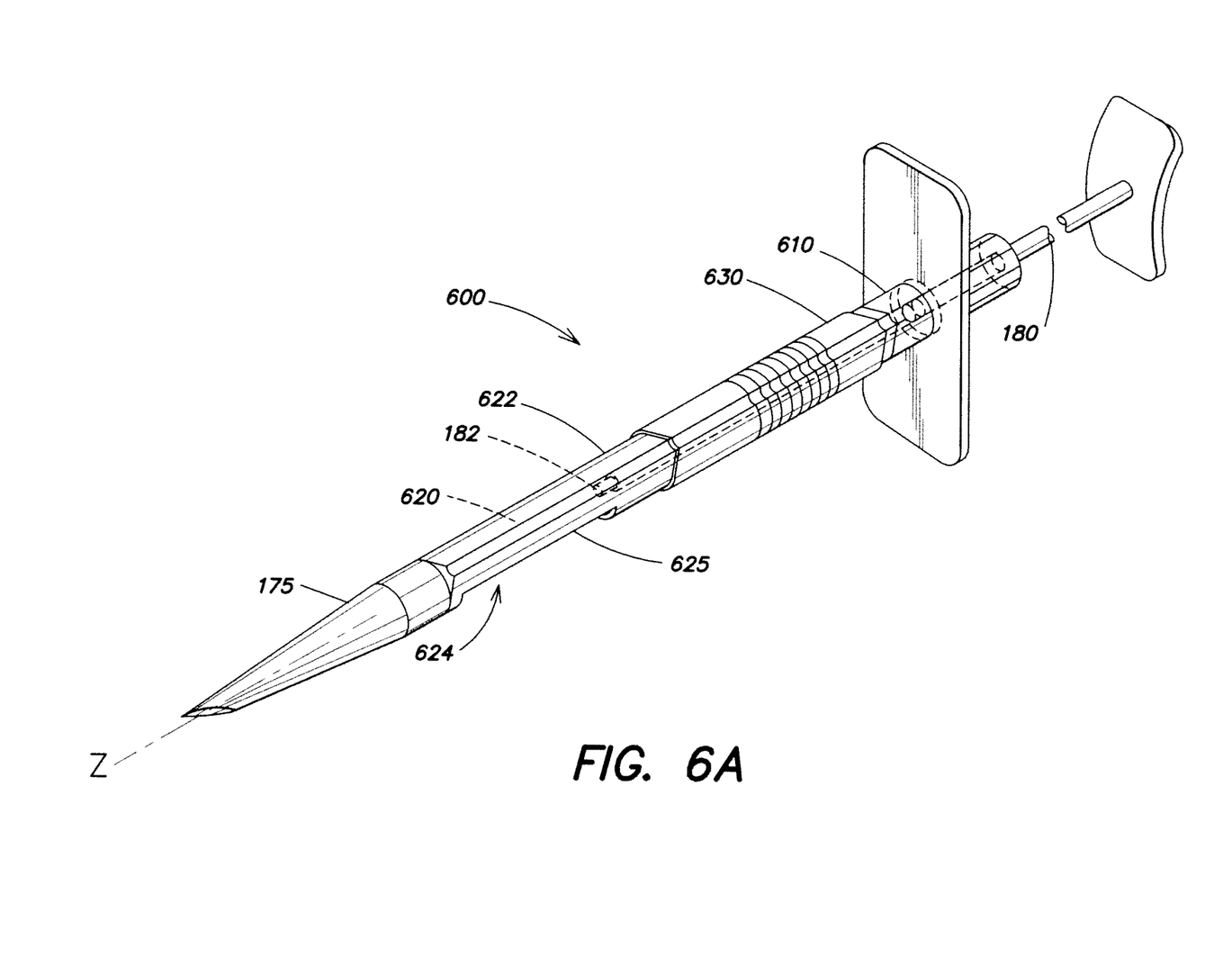
FIG. 6A is a perspective view of a second exemplary embodiment of an injector according to aspects of the present invention having an open loading chamber.

FIG. 6A is a perspective view of a second exemplary embodiment of an IOL injector 600 according to aspects of the present invention. As illustrated in FIG. 6A, the injector has an open loading chamber 620. Injector 600 comprises an injector body 610 defining a lumen extending along a longitudinal axis Z. The injector has an opening 624 to the loading chamber that is defined at least in part by a tapered edge 625 extending in the direction of longitudinal axis Z.

Figure 8A:
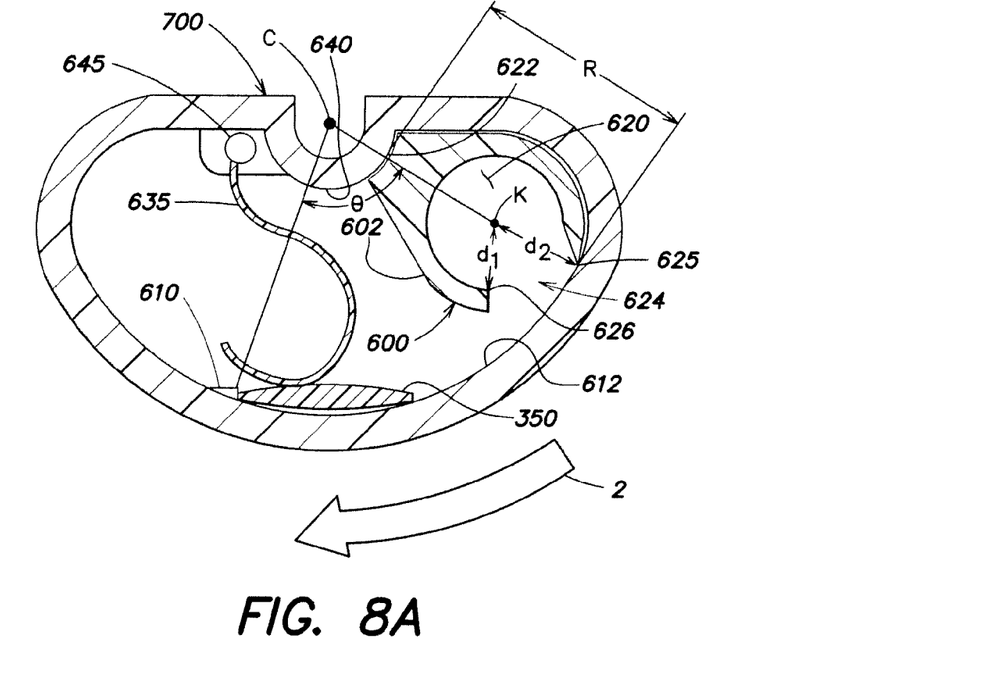
FIGS. 8A-8B illustrate steps for loading an injector according to aspects of the present invention.

Tapered edge 625 is illustrated in the cross-sectional view of injector 600 in FIG. 8A. As illustrated in FIG. 8A, in some embodiments, the lumen has a substantially circular cross section. However, the lumen may be elliptical or oval. In some embodiments, having a substantially circular cross section, it is advantageous that tapered edge 625 be located further from a center K of the substantially circular lumen (i.e., a distance $d_2$ from K) than an opposing edge 626 of opening 624 (i.e., a distance $d_2$ from K) thereby facilitating loading a lens by scooping the lens into the loading chamber as described below. In some embodiments, regardless of the shape of the lumen, tapered edge 625 is located further from the middle of surface 622 than opposing edge 626. It is to be appreciated that tapered edge 625 may be sharp. It is also to be appreciated that to be sharp, an edge need not come to point at a microscopic level.

Figure 6B:
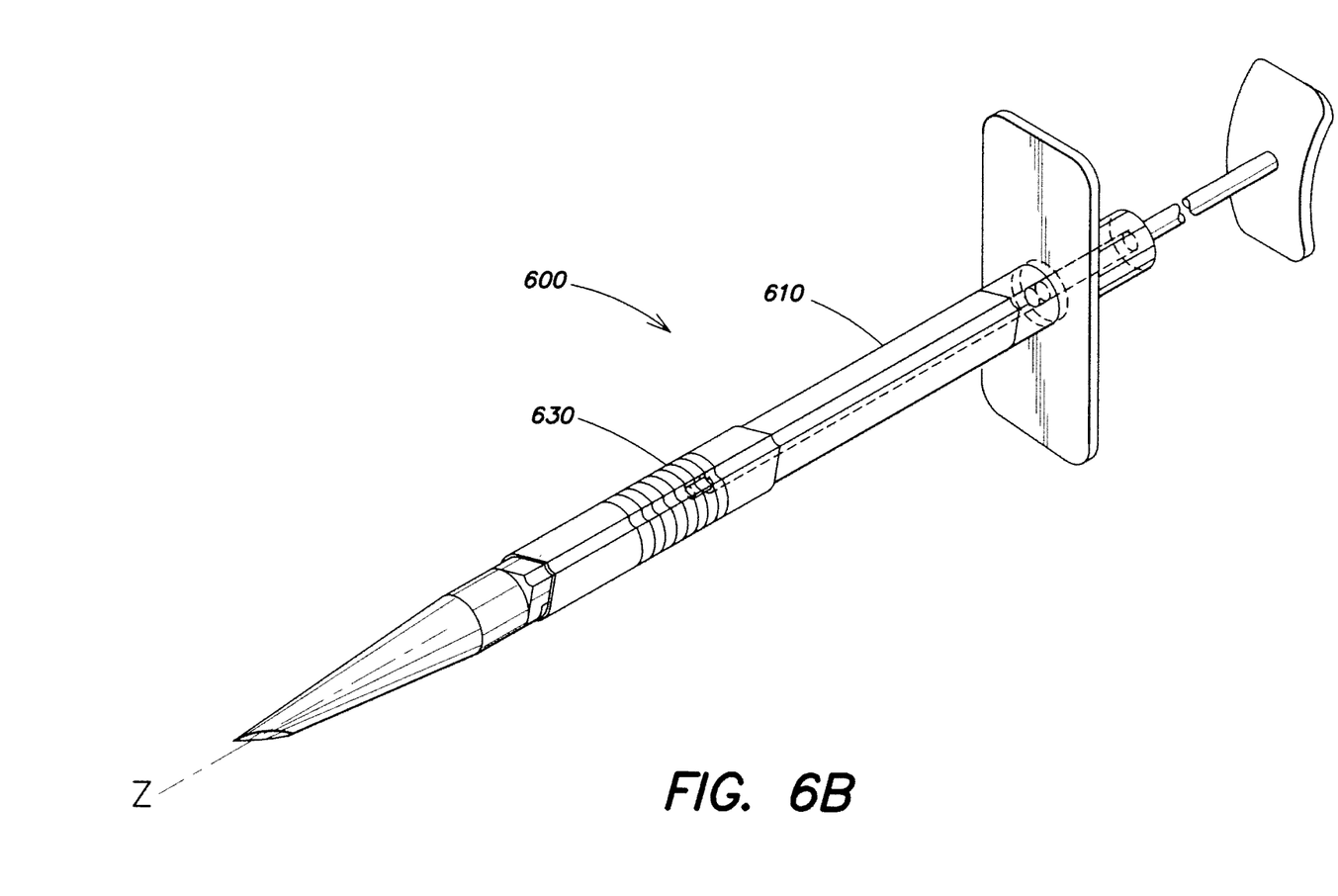
FIG. 6B is a perspective view of the second exemplary embodiment of the injector according to aspects of the present invention having a closed loading chamber.
Figure 6C:
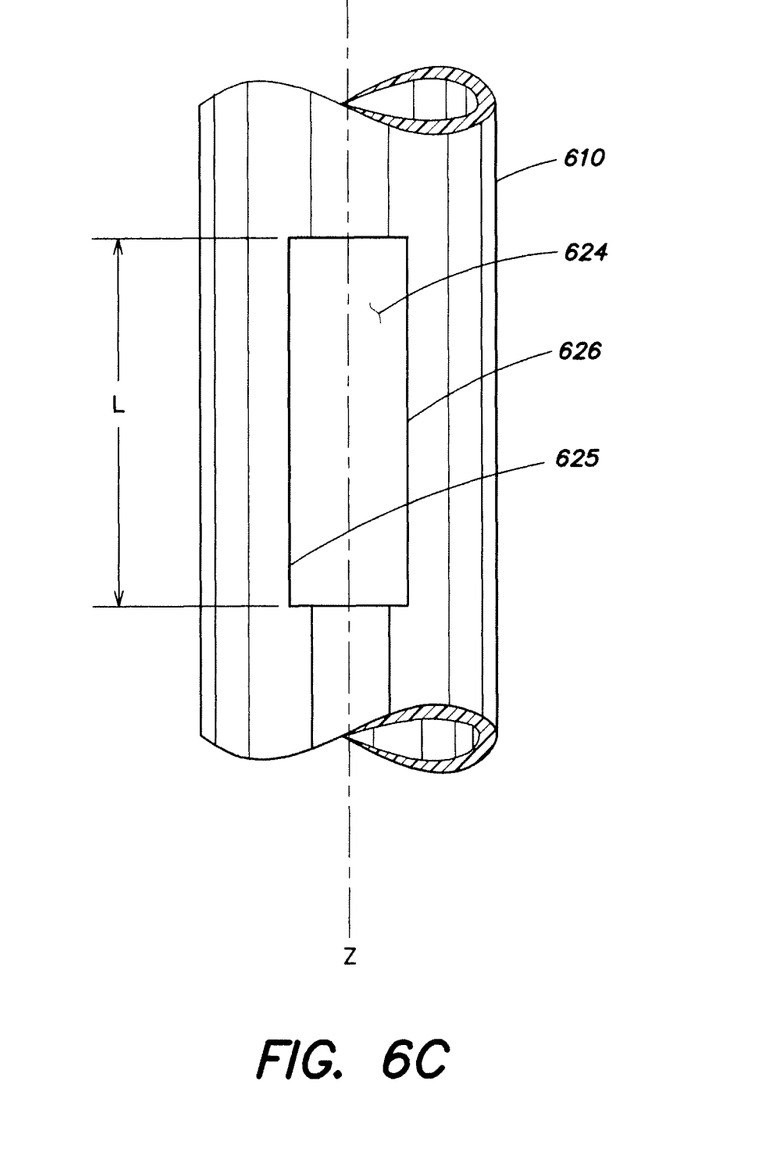
FIG. 6C is a side view of the second exemplary embodiment illustrating a loading chamber opening.

Referring to FIG. 6C, opening 624 is illustrated in a side view of injector 600. The length of tapered edge 625 can extend along the entire length L of opening 624 (e.g., the opening may be rectangular and the tapered edge may extend along a side of the rectangle) or the tapered edge can extend along only a portion of length L that is adequate to engage an IOL in the manner discussed below with reference to FIGS. 8A and 8B. It is also to be appreciated that tapered edge 625 can be aligned parallel to axis Z; however, tapered edge 625 may be disposed other than parallel so long as it extends at least some distance along the direction of axis Z. In some embodiments, only edge 625 is tapered and edge 626 is non-tapered.

Referring again to FIG. 6A, in some embodiments, injector 600 may have an exterior surface 622 that is configured to facilitate loading of a lens into the injector in a manner as discussed below with reference to FIGS. 8A and 8B. Injector tip 175 may be integrated with injector body 610 or may be attachable to the body using any suitable technique.

As illustrated in FIGS. 6A and 6B, a door 630 may be provided which can be closed to maintain a lens within the loading chamber of the injector 600. Although the illustrated door is configured and arranged to slide along injector body 610 into a closed position, the door may be disposed on a hinge or may simply snap into a closed position. Plunger 180 is aligned in the lumen such that tip 182 advances the lens after it has been obtained in the injector. The tip may be conventional fork shaped tip or a soft silicone tip as is known in the art.

Figure 7:
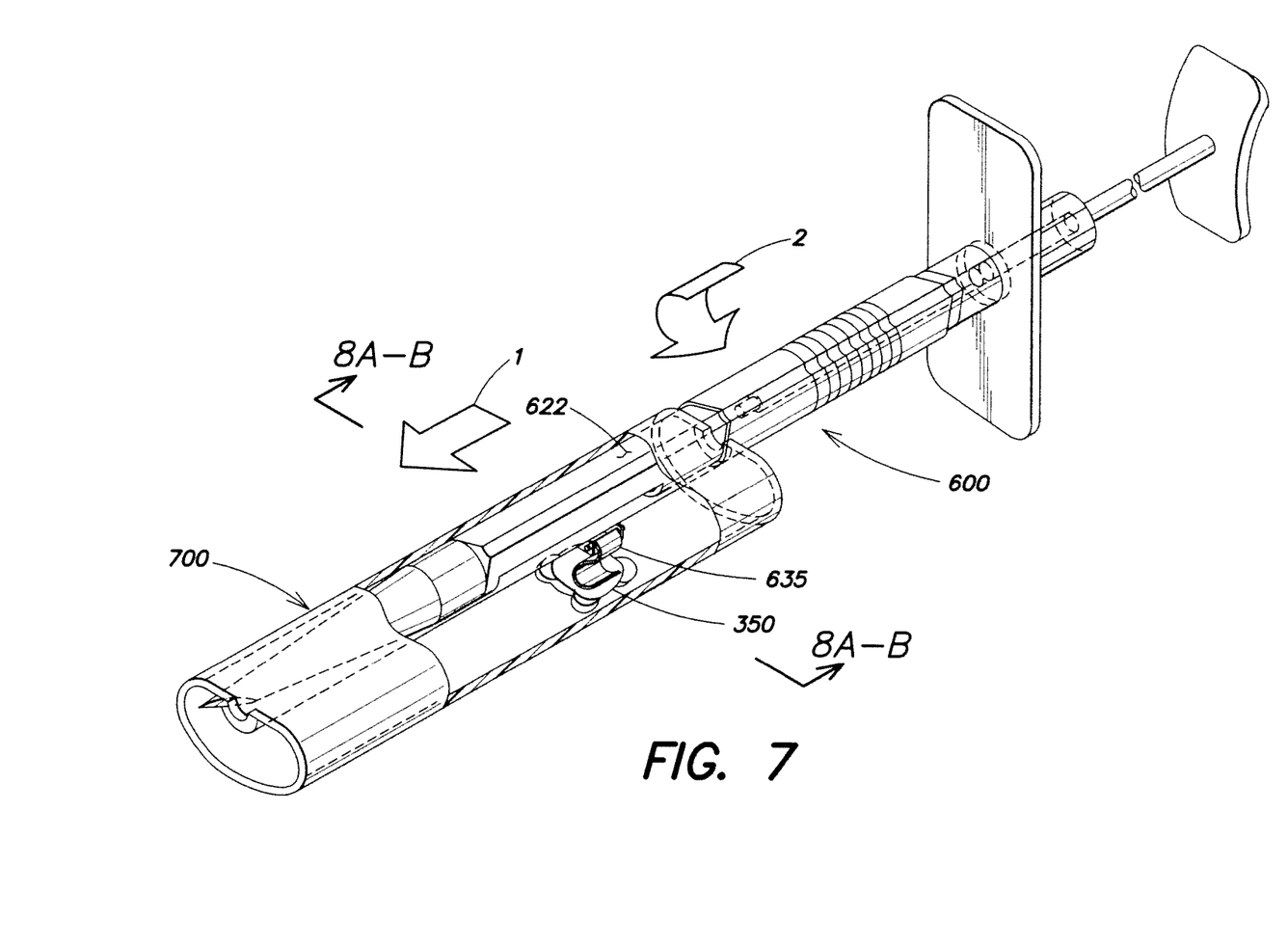
FIG. 7 is a perspective view of the second exemplary embodiment of an injector as illustrated in FIG. 6A engaged with a second exemplary embodiment of a vial, in which a portion of the vial is broken away.

FIG. 7 is a perspective view of the second exemplary embodiment of an injector as illustrated in FIG. 6A that is engaged with a second exemplary embodiment of an IOL vial 700. As discussed in greater detail with reference to FIGS. 8A and 8B, injector 600 can be inserted (in the direction indicated by arrow 1) into vial 700; and the injector body can be rotated relative to the vial (in the direction indicated by arrow 2) to obtain the IOL in the IOL injector body. In some embodiments, the injector is rotated about a curved interior surface 640 of the vial by contacting surface 640 with at least a portion of surface 622 of the injector.

Figure 8B:
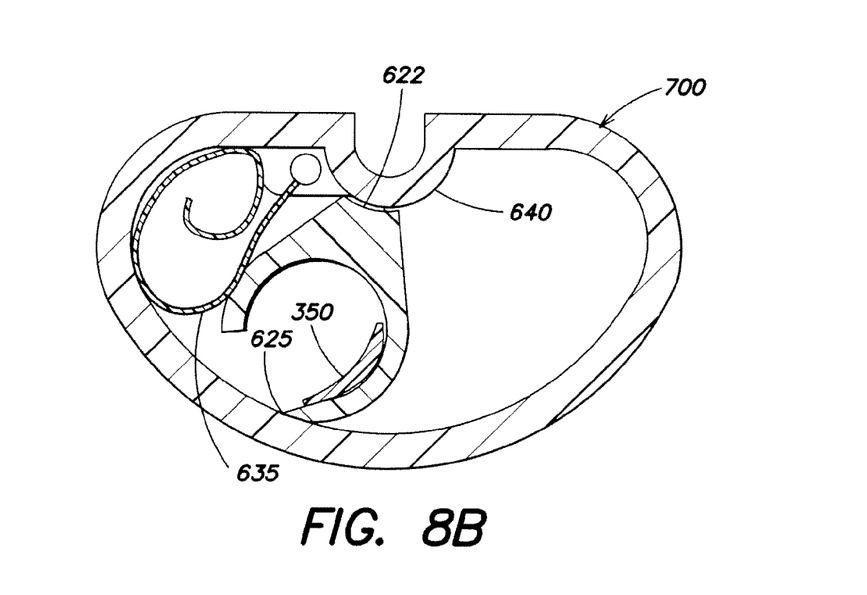

FIGS. 8A-8B are cross-sectional views taken along line 8A-B of FIG. 6A that illustrate steps for loading an injector according to aspects of the present invention. As discussed above, injector 600 is inserted into vial 700. Vial 700 is provided with a flexible arm 635 adapted to maintain an IOL 350 against a surface of the vial. Injector 600 may be rotated relative to the vial to obtain the IOL in the IOL injector body.

In some embodiments, a portion of an interior surface of the vial is selected to conform to an exterior surface of the injector in a region proximate opening 624. For example, in some embodiments surface 622, which may be located on a substantially opposite side of injector 600 from opening 624, has concave curvature that substantially matches a convexly curved interior surface 640 of vial 700 (e.g., they have substantially the same radius of curvature and may share a center of curvature C). Accordingly, injector 600 can be rotated about center of curvature C (i.e., in the direction of arrow 2) in a stable and reliable manner. In some embodiments, surface 622 is convex and surface 640 is concave.

In some embodiments, the distance R from surface 622 to tapered edge 625 is substantially equal to the distance from vial surface 640 to vial surface 612 (e.g., over an angle θ), such that the inserter 600 remains contained between surfaces 640 and 612 upon rotation, thereby adding to the stability and reliability of the rotation of inserter 600. It is to be appreciated that flexible arm 635 maintains IOL 350 against a surface disposed opposite curved surface 640. Although flexible arm 635 is illustrated having a hook shaped cross section, any suitable shape may be employed. For example an arm having a simple straight shape that collapses upon the application of sheer force as would occur when the inserter is rotated about the curved surface 640 and thereby contacts a side of the flexible arm. Flexible arm 635 may be attached to the vial base at location 645 using a hinge or other suitable rotatable structure, or the flexibility of flexible arm may be selected such that the flexible arm folds or wraps around location 645 upon contact with the injector without the use of a hinge.

As illustrated in FIG. 8B, injector 600 may be rotated relative to the vial in the manner described above (i.e., with surface 622 of the inserter contacting surface 640 of the vial) to obtain the IOL in the IOL injector body. Upon rotation of the inserter about center of curvature C, tapered edge 625 engages lens 350 and in a shovel-like manner lifts the lens into the loading chamber. A stop 610 may be located to hold the lens in place as the lens is contacted by the tapered edge. It is to be appreciated that the curved shape of the interior of the loading chamber causes the lens to fold the IOL as the IOL encounters the interior surface of the lumen. As the lens is engaged by the tapered edge, a portion of the inserter 602 engages flexible arm 625 thereby moving the flexible arm out the way as illustrated in FIG. 8B.

It is to be appreciated that although in some application is advantageous to provide and/or use injector 600 with a vial 700, injector 600 may be used with any suitable structure capable of maintaining an IOL such that the tapered edge 625 can be used to interact with the IOL in a manner such that the IOL is obtained in loading chamber 620.

Figure 9:
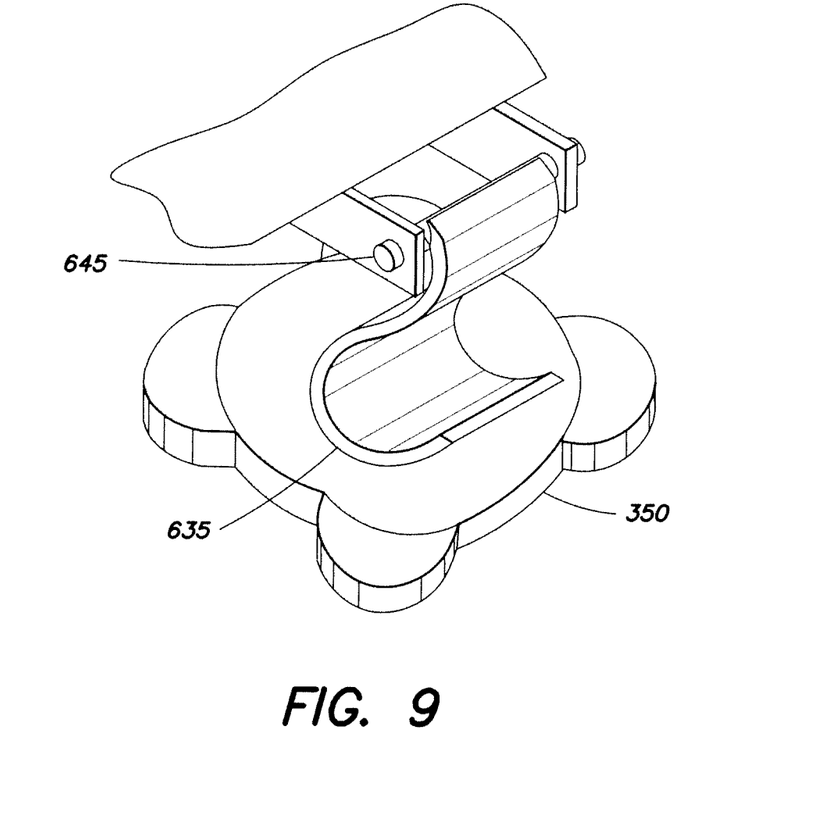
FIG. 9 is a perspective view of an exemplary embodiment of a flexible arm.

FIG. 9 is a perspective view of an embodiment of a flexible arm 635 illustrating further details of the flexible arm. The arm is configured to maintain lens 350 against a wall of the vial as discussed above, and flexible enough such that the movement about attachment 645 allow arm to be moved away from lens 350 during loading as discussed above with reference to FIG. 8B. The arm preferably has a shape such that contact with the lens is made over a substantial area to avoid damage to the lens. Preferably, the portion of the arm contacting the lens is smooth to facilitate movement away or sliding along the lens without causing damage.

Injectors and vials as described herein are preferably made from a biocompatible and sterilizable material. For example, the injector and/or vial (including the flexible arm) may be made of polypropylene or polyetherimide (e.g. Ultem™ available from General Electric Corp.). In some embodiments, it is advantageous if the material used for an injector and/or vial is transparent to facilitate viewing of the lens during loading.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An IOL injector body and a vial in a combination, the IOL injector body having a lumen with a lumen longitudinal axis, and the IOL injector comprising:
   an injector body segment defining a portion of the lumen;
   a first loading chamber component coupled to the injector body segment;

a second loading chamber component comprising a lens contact surface, the second loading chamber component being hingedly coupled to the first loading chamber component such that the second loading chamber component is capable of rotating about a second axis that is parallel to the lumen longitudinal axis; and the vial comprising a vial base and a removable cover, the vial base comprising a cylindrical wall and a bottom surface that define a volume capable of holding a liquid, the cylindrical wall defining a vial central longitudinal axis, an IOL-holder mount connected to the vial base and disposed in said volume, the IOL-holder mount maintaining an IOL holder having an IOL attached thereto, the IOL-holder mount configured to permit displacement of the IOL-holder towards the bottom surface, and an injector guide rotatably mounted in said volume such that the injector guide can rotate about the vial central longitudinal axis, the injector guide configured to permit the injector body to be inserted into the vial along the injector guide to displace the IOL-holder toward the bottom surface.

2. The injector of claim 1, wherein the second loading chamber component is configured and arranged such that, upon rotation of the second loading chamber about the second axis, the first loading chamber component and the second loading chamber component combine to form a second portion of the lumen.

3. The IOL injector of claim 2, the first and second loading chamber components form a rotationally complete portion of the lumen.

4. The injector of claim 1, wherein the second loading chamber component is configured and arranged to fold an IOL using the lens contact surface upon rotation about the second axis.

5. The injector of claim 4, wherein the second loading chamber component is configured and arranged to fold the IOL such that after rotation the lens is ready for delivery.

6. The injector of claim 1, wherein the second axis is aligned with a wall of the injector body.

7. The injector of claim 1, wherein the first loading chamber component is rigidly connected to the injector body.

8. The injector of claim 1, wherein the first loading chamber component is integrally formed with the injector body.

9. The injector of claim 1, wherein the first loading chamber component and the second loading chamber component are configured to form a loading chamber in a closed position.

10. The injector of claim 9, wherein the first loading chamber component and the second loading chamber component are configured to snap together.

* * * * *